April 14, 1959 F. RAHBEK Plant Pat. 1,826
FICUS PANDURATA
Filed Jan. 23, 1957
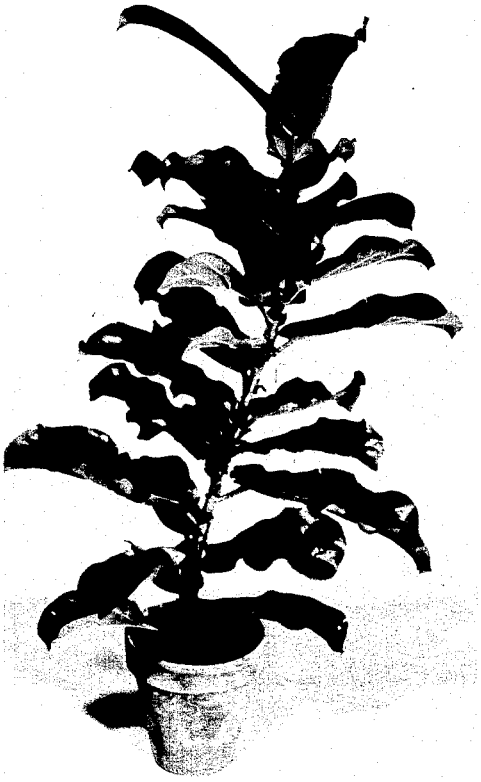
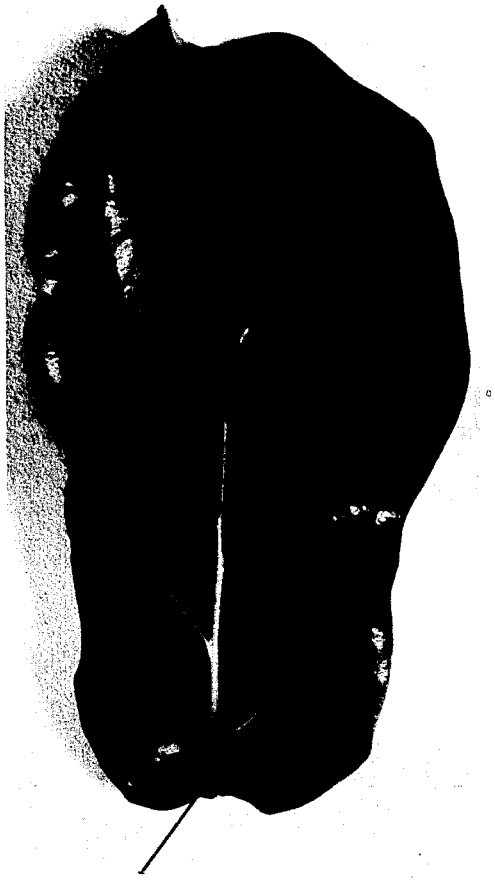
Inventor:
Frode Rahbek
by Howson & Howson
Attys.

United States Patent Office

Plant Pat. 1,826
Patented Apr. 14, 1959

1,826

FICUS PANDURATA

Frode Rahbek, Primos, Pa., assignor to Robert Craig Company, Norwood, Pa., a corporation of Pennsylvania Application January 23, 1957, Serial No. 635,927

1 Claim. (Cl. 47—59)

The present invention relates to a new and distinct variety of *Ficus pandurata* plant.

This new variety of *Ficus pandurata* plant was discovered by the applicant as a sport growing in a cultivated nursery bed in Norwood, Delaware County, Pennsylvania; and has been asexually reproduced many times by the applicant by layering at Norwood, Delaware County, Pennsylvania.

The outstanding characteristic of this plant resides principally in its general overall appearance, being much shorter and bushier than the conventional *Ficus pandurata*. In addition, the stem of this plant is extremely short noded, as compared with the conventional *Ficus pandurata*; the nodes being spaced apart approximately one quarter of the distance of the conventional *Ficus pandurata*, and spaced apart uniformly in the full grown portion of the plant. Another outstanding characteristic of this plant is that the full grown leaves on a single plant do not vary in size to any great extent from one another but are of a generally uniform size, while in a conventional *Ficus pandurata* the full grown leaves may vary between approximately sixteen inches in length to more than two feet in length. Further, the mature leaves of the plant of the present invention are of a much deeper and darker green color and of a more uniform color than the leaves of the conventional *Ficus pandurata* with the result that the lighter veins of the leaf form a sharp contrast with the leaf and are outstanding in appearance. These above characteristics, in combination, provide a plant which has a more uniform contour and color than the conventional *Ficus pandurata*, is shorter and bushier than the conventional *Ficus pandurata*, and in general is a plant of a much neater and pleasing appearance.

The accompanying drawings illustrate a full grown *Ficus pandurata* plant of the present invention which is approximately three years old, and a mature leaf from the plant.

The following detailed description of the *Ficus pandurata* plant of the present invention refers to color plates of "A Dictionary of Color" by A. Maerz and M. Rea Paul, first edition, 1930.

The plant has a single central main stem of a generally rough texture and of a color at the bottom portion equivalent of that of plate 56–E–1, with the color changing gradually to plate 19–K–5 in the new grown portion of the stem, passing through 15–H–6 and 22–J–6. The stem has nodes out of which the leaves grow uniformly spaced approximately one and one-half to two inches apart along the matured portion thereof, while in the new grown portion the nodes are somewhat closer together; and the stalk in a mature three year old plant is approximately one-half to five-eighths of an inch in diameter at its base and tapers uniformly inward to the top portion. In a mature three year old unpruned plant of the present invention, the stalk is approximately thirty to forty inches tall and is generally straight.

The leaves are arranged alternately about the stalk axis with one leaf growing out of each node. The leaves are generally fiddle-shaped or banjo-shaped, being wider at their outer portion than at their inner portion and range, in length, from approximately twelve to fifteen inches. The side edges of the leaves are wavy or undulating. The leaves vary from four to five inches across at their widest portion and vary from two and one-half to three and one-half inches in width at their narrow or necked inner portion. The upper surface of each leaf is glossy or wax-like while the under surface is dull.

With the exception of the new grown leaves, the coloring of the leaves is extremely uniform throughout the plant, the stem of each leaf is of a color equal to that of plate 21–K–11, while the veins of the leaves are of a color equivalent to 20–L–4. The upper surface of the leaves is of a color equal to 31–A–12, while the under side of the leaves is 22–L–4.

The new grown leaves are much lighter in color than the mature leaves of the plant. The upper surface of the new grown leaves is of a color equal to that of plate 18–L–9, while the under side is equal to that of plate 19–L–6.

The new variety of *Ficus pandurata* of the present invention is distinguished primarily by its small bushy appearance and uniform leaves.

I claim:

A new and distinct variety of *Ficus pandurata* plant substantially as shown and described, characterized particularly as to novelty by its short-noded stem, and its uniformly sized and shaped leaves of a uniform color, providing a short, bushy plant.

No references cited.